United States Patent
Gharda (10) Patent No.: US 9,617,207 B2
(45) Date of Patent: Apr. 11, 2017

(54) METHOD FOR PREPARATION OF PERFLUOROALKYL SULFENYL CHLORIDE

(76) Inventor: Keki Hormusji Gharda, Mumbai (IN)

(*) Notice: Subject to any disclaimer, the term of this patent is extended or adjusted under 35 U.S.C. 154(b) by 874 days.

(21) Appl. No.: 13/541,286

(22) Filed: Jul. 3, 2012

(65) Prior Publication Data
US 2012/0296119 A1 Nov. 22, 2012

Related U.S. Application Data

(63) Continuation of application No. PCT/IN2010/000385, filed on Jun. 8, 2010.

(30) Foreign Application Priority Data

Jan. 4, 2010 (IN) .............................. 6/MUM/2010

(51) Int. Cl.
| | | |
|---|---|---|
| C07C 313/00 | (2006.01) | |
| C07C 19/01 | (2006.01) | |
| C07C 313/08 | (2006.01) | |
| C07C 319/14 | (2006.01) | |
| B01J 8/20 | (2006.01) | |
| B01J 19/00 | (2006.01) | |
| B01J 19/18 | (2006.01) | |
| B01F 5/10 | (2006.01) | |
| B01F 7/00 | (2006.01) | |
| B01F 7/18 | (2006.01) | |
| B01F 15/06 | (2006.01) | |
| B01F 3/12 | (2006.01) | |

(52) U.S. Cl.
CPC .......... *C07C 313/08* (2013.01); *B01F 3/1271* (2013.01); *B01F 5/10* (2013.01); *B01F 7/00633* (2013.01); *B01F 7/18* (2013.01); *B01F 15/066* (2013.01); *B01J 8/20* (2013.01); *B01J 19/0066* (2013.01); *B01J 19/1881* (2013.01); *C07C 319/14* (2013.01); *B01F 2015/061* (2013.01); *B01J 2219/00063* (2013.01); *B01J 2219/00065* (2013.01); *B01J 2219/00081* (2013.01)

(58) Field of Classification Search
CPC .............................. C07C 19/01; C07C 313/00
USPC .................................................. 562/821, 835
See application file for complete search history.

(56) References Cited

U.S. PATENT DOCUMENTS

| | | | |
|---|---|---|---|
| 2,884,453 A | 4/1959 | Tullock | |
| 5,087,747 A | 2/1992 | Bielefeldt et al. | |
| 6,225,505 B1 * | 5/2001 | Kimura | C07C 319/14 |
| | | | 568/38 |

FOREIGN PATENT DOCUMENTS

| | | |
|---|---|---|
| AU | 2010100307 A4 | 6/2010 |
| CN | 101492403 A | 7/2009 |
| DE | 274821 A1 | 1/1990 |

OTHER PUBLICATIONS

Russian Chemical Reviews, 61, 517-536 (1992).*
Sizov et al., Russian Chemical Reviews, 61, 517-536 (1992).*
Basta, http://www.chemicalprocessing.com/articles/2003/102/.*
Sizov et al., "Polyfluoroalkanesulphenyl chlorides," Russian Chemical Reviews, 61 (5), pp. 517-536 (1992).
Kühle, "One Hundred Years of Sulfenic Acid Chemistry I. Sulfenyl Halide Syntheses," Synthesis International Journal of Methods in Synthetic Organic Chemistry, vol. 11, pp. 561-562, (Nov. 1970).
Clark and Tavener, "The preparation of trifluoromethyl aryl sulfides using KF and thiophosgene," Journal of Flourine Chemistry, 85, pp. 169-172 (1997).
Tavener et al., "Trifluoromethylthiolation of aromatic substrates using thiophosgene-fluoride salt reagents, and formation of byproducts with multi-carbon chains," Journal of Flourine Chemistry, 95, pp. 171-176 (1999).
International Search Report for PCT/IN2010/000385 (in English) mailed Dec. 2, 2010; ISA/CN.
Thoai Nguyen et al. "Reaction of Perfluoroalkyl Carbanions with Thiocyanates, Synthesis of Fluorinated Sulfides and Sulfenyl Chlorides." J. Org. Chem. vol. 46, No. 9. Apr. 1, 1981. pp. 1938-1940.

* cited by examiner

*Primary Examiner* — Sudhakar Katakam
*Assistant Examiner* — Sonya Wright
(74) *Attorney, Agent, or Firm* — Harness, Dickey & Pierce, P.L.C.

(57) ABSTRACT

The present disclosure provides a process for the preparation of perfluoroalkyl sulfenyl chloride by reacting a compound of formula [I] with at least one fluoride compound and thiophosgene.

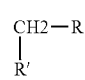

[I]

17 Claims, 1 Drawing Sheet

METHOD FOR PREPARATION OF PERFLUOROALKYL SULFENYL CHLORIDE

CROSS-REFERENCE TO RELATED APPLICATIONS

This application is continuation of International application No. PCT/IN2010/000385, filed Jun. 8, 2010. This application claims priority to Indian Application No. 6/MUM/2010, filed Jan. 4, 2010. The disclosure(s) of the above applications are incorporated herein by reference.

FIELD

The present disclosure relates to a method for the preparation of perfluoroalkyl sulfenyl chloride, which is used as an intermediate for the preparation of insecticides and pharmaceuticals.

BACKGROUND

Perfluoroalkane sulfenyl chlorides are important group of chemicals used in pharmaceutical and agrochemical industries. In the preparation of perfluoroalkyl sulfenyl chloride, the reaction involves two phases such as solid potassium fluoride in polar solvent and the thiophosgene. The solid-liquid phase reaction requires critical reaction conditions to initiate the reaction and consequently gives the requisite conversion and resulting in higher yield. Thus, the mixing of solid liquid reactants is vital aspect of the process.

Fluoro-compounds are characteristically difficult to synthesize. The reactivity of fluorine is such that it is difficult or impossible to directly prepare fluoro derivatives. The process for the preparation of fluoro derivatives involves reacting a halogen compound, generally a chloro derivative and exchanging the halogen with an inorganic fluoro compound, generally an alkali metal fluoride, hydrogen fluoride and the like.

EXISTING KNOWLEDGE

A review on perfluoroalkanesulfenyl chlorides is disclosed in the *Russian Chemical Reviews*, 61, 940-977 (1992).

A process for the preparation of trifluromethanesulfenyl chloride in which a mixture of sodium fluoride, trichloromethanesulfenyl chloride and tetramethylene sulfone is heated at 150° C. is disclosed in '*Synthesis Journal*', page 561-562, volume 11, 1970.

Use of potassium fluoride (KF) and thiophosgene for the synthesis of trifluoromethanethiolate is disclosed in Journal of Flourine Chemistry, 85, (1997), 169-172.

method for preparation of trifluoromethanethiolates by reaction of tetramethylammonium fluoride and thiophosgene at low temperatures is disclosed in *Journal of Flourine Chemistry*, 95, (1999), 171-176.

U.S. Pat. No. 2,884,453 discloses a process of preparing the compounds containing the trifluoromethylthio radical. The process involves reacting an alkali metal fluoride with thiocarbonyl chloride of formula CSCln, where n is 2 or 4 under substantially anhydrous condition.

U.S. Pat. No. 5,087,747 discloses a process for the preparation of trifluoromethylsulfenyl chloride by reacting bis-(-trifluromethyl)disulfane in the liquid phase with chlorine in the presence of strong acid at a temperature of about 18 to 120° C.

U.S. Pat. No. 6,225,505 describes a process for producing a trifluromethylthiomethylbenzene derivative, in which potassium fluoride and thiophosgene are employed.

German Patent No. 274821 discloses a process for the preparation of trichloromethyl sulfenyl chloride which is carried out using chromium-based catalyst and hydrogen fluoride (HF) at a very high temperature in vapor phase. The process disclosed in the German patent No 274821 involves use of HF at elevated temperature. It renders the process inherently dangerous and unsafe as HF is extremely difficult to handle at such temperature and thus the process is commercially unattractive.

Thus there is a need for a process for the preparation of perfluoroalkyl sulfenyl chloride which is simple, high yielding, safe, easy to operate on commercial scale and cost-effective.

OBJECTS

Some of the objects of the present disclosure, which at least one embodiment herein satisfies, are as follows:

It is an object of the present disclosure to provide a process for the preparation of trifluoromethyl thiomethyl benzene derivative.

It is another object of the present disclosure to provide a process for the preparation of perfluoroalkyl sulfenyl chloride.

It is still another object of the present disclosure to provide a process for improving the reaction conditions such as temperature and mixing of solid and liquid phase by employing specially designed grinding beads.

It is yet another object of the present disclosure to provide a process for the preparation of perfluoroalkyl sulfenyl chloride which is simple, safe, convenient, easy to operate on commercial scale and cost-effective.

It is a further object of the present disclosure to provide a process for the preparation of perfluoroalkyl sulfenyl chloride which provides highly pure product with high yield.

Other objects and advantages of the present disclosure will be more apparent from the following description when read in conjunction with the accompanying figures, which are not intended to limit the scope of the present disclosure.

SUMMARY

In accordance with the present disclosure there is provided a process for the preparation of perfluoroalkyl sulfenyl chloride; said process comprising the following steps:

a. reacting a compound of formula [I]

wherein R represents an aromatic group, with or without a substituent; and R' is at least one selected from the group consisting of fluorine, chlorine, bromine and iodine; with at least one fluoride compound selected from the group consisting of potassium fluoride, potassium bifluoride, sodium fluoride, tetramethylammonium fluoride and benzyltrimethylammonium fluoride and thiophosgene in a solvent selected from the group consisting of acetonitrile, dichloromethane, sulfolane and carbon tetrachloride, to obtain a reaction mass containing trifluoromethyl thiomethyl benzene derivative;

b. pulverizing the reaction mass with the help of beads and isolating the trifluoromethyl thiomethyl benzene derivative from the reaction mass;

c. distilling the trifluoromethyl thiomethyl benzene derivative to obtain a purified trifluoromethyl thiomethyl benzene derivative;

d. dissolving the purified trifluoromethyl thiomethyl benzene derivative in a solvent selected from the group consisting of dichloromethane, toluene, benzene, ethylene dichloride, mono chloro benzene, carbon tetra chloride, ortho-dichloro benzene and tri chloro benzene; and e. cleaving the trifluoromethyl thiomethyl benzene derivative by selective chlorinolysis by passing chlorine gas at a temperature in the range of about −10° C. to about 50° C. to obtain a perfluoroalkyl sulfenyl chloride.

Typically, the aromatic group is at least one selected from the groups consisting of aromatic hydrocarbon, heterocyclic aromatic and polycyclic aromatic hydrocarbon.

Typically, the aromatic hydrocarbon is at least one selected from the group consisting of benzene, toluene, o,p,m-xylene, benzophenone, substituted benzophenone, acetophenone, substituted acetophenone, tri methyl benzene, tetra methyl benzene and penta methylbenzene.

Typically, the heterocyclic aromatic is at least one selected from the group consisting of furan, pyridine, pyrazine, imidazole, pyrazole, oxazole and thiophene.

Typically, the polycyclic aromatic hydrocarbon is at least one selected from the group consisting of naphthalene, anthracene and phenanthrene.

Typically, the compound of formula I is at least one selected from the group consisting of ortho-chlorobenzyl chloride, para-chlorobenzyl chloride, 4-chloromethyl methylene dioxy benzene, 1-chloromethyl naphthalene, bis-2,4-chloromethyl toluene, tris 2,4,6-chloromethyl toluene, bis-9,10-chloromethyl anthracene and a mixture thereof.

Preferably, the solvent employed in step (a) is at least one selected from the group consisting of acetonitrile and sulfolane.

Typically, the trifluoromethyl thiomethyl benzene derivative is selected from the group consisting of ortho-chlorobenzyl trifluoromethyl sulphide, para-chlorobenzyl trifluoromethyl sulphide, 3,4-dioxy methylene benzyl trifluoromethyl sulfide, 1-naphthalene methyl trifluoromethyl sulfide, toluene-bis-2,4-methyl trifluoromethyl sulfide, toluene-tris-2,4,6-methyl trifluoromethyl sulfide and anthracene-bis 9,10-methyl trifluoromethyl sulfide.

Preferably, the solvent employed in step (d) is at least one selected from the group consisting of dichloromethane and ethylene dichloride.

Preferably, the cleaving of trifluoromethyl thiomethyl benzene derivative is carried out at a temperature in the range of about −5° C. to 50° C.

Preferably, the perfluoroalkyl sulfenyl chloride is trifluoromethylsulfenyl chloride.

Typically, the yield of perfluoromethyl sulfenyl chloride is at least 94%.

Typically, the beads are selected from the group consisting of glass beads, sand beads, stainless steel beads, titanium beads and zirconium oxide beads.

Typically, the size of the beads is in the range of about 0.5 mm to about 10 mm, preferably, the size of the beads is in the range of about 0.5 mm to about 3 mm.

Typically, the proportion of beads employed in the reaction is 0.25 kg to 1 kg per mole of compound of formula I.

Typically, the shape of the beads is selected from the group consisting of spherical, oval and round.

Typically, the proportion of fluoride compound used is about 3.6 mole to 6.0 per mole of compound of formula I.

Typically, the proportion of thiophosgene is about 1.2 mole to 2.0 mole per mole of compound of formula I.

In accordance with another aspect of the present disclosure there is provided a system for the preparation of perfluoroalkyl sulfenyl chloride; said system comprising:

a. a reactor comprising:
  i. an inlet means for facilitating entry of reactants into the reactor;
  ii. an outlet means for facilitating exit of final product out of the reactor;
  iii. a stirrer means for mixing the reactants contained inside the reactor;
  iv. a cooling means for preventing overheating of the reactants;
  v. a temperature measuring and indicating means for measuring and indicating the temperature of the resulting mixture of the reactants contained inside the reactor; and
  vi. a pressure gauge for measuring pressure generated inside the reactor;
b. a pump for moving the resulting mixture contained inside the reactor; and
c. a milling device for pulverization of the resulting mixture moved from the gear pump, wherein said pulverized mixture enter into the reactor for further mixing thereof; and wherein said final product formed after subsequent mixing is exited through the outlet means of the reactor.

Typically, the milling device is a bead mill, said bead mill comprising a plurality of beads adapted to pulverize said resulting mixture moved from the pump.

BRIEF DESCRIPTION OF THE ACCOMPANYING DRAWING

The present disclosure will now be described with reference to the accompanying drawing in which.

DETAILED DESCRIPTION

In the preparation of perfluoroalkanesulfenyl chloride the reaction involves two phases such as solid potassium fluoride in polar solvent and thiophosgene. The solid-liquid phase reaction requires critical reaction conditions to achieve higher yield. Thus, the mixing of the solid and liquid reactants is crucial and important aspect of the process for initiation and completion of the reaction.

From the prior art it is evident that the methodology of preparing trifluromethanethiolate, trifluoromethyl thiolation has been carried out using various activated aromatic substrates both at the nucleus as well as in the side chain including substituted and activated pyridines.

The nucleophillic substitution of activated halogen in the aromatic nuclei as well as in the side chain takes place readily with the in-situ generated trifluoromethanethiolate anion at a temperature varying from −40° C. to reflux.

Most of the prior art processes involves use of fluoride compounds like hydrogen fluoride, potassium fluoride and alkali fluorides for preparation of perfluoroalkyl sulfenyl chloride. Thus, it inherently has certain drawbacks in using such fluoride compounds. Reactants such as hydrogen fluoride in liquid form or diluted with dipolar aprotic solvents are also used. However, hydrofluoric acid is too powerful or harsh reactant and often results in unwanted polymerization and other side reactions.

In this event and especially in the case where it is desired to obtain the derivatives which are fluorinated on a carbon atom of an alkyl radical rendered electron-deficient by the presence of electron-withdrawing groups, this art is faced with an alternative which is not encouraging; either very harsh conditions are selected and reaction goes on uncontrolled or mild reaction conditions are adopted wherein reactants do not get fully converted into the products.

Another disadvantage is the selectivity of the reaction: when there is more than one halogen to be exchanged on the same carbon atom, it is often difficult to exchange less than all of it.

It is surprisingly found that trifluoromethylthiolation of the side chain of halogenated aromatic substrates readily takes place by using a combination of inorganic fluoride compounds like alkali fluorides, more particularly sodium, potassium, lithium, Cesium and potassium bifluoride ($KHF_2$).

In addition, organic fluoride compounds like tetramethylammonium fluoride, tetramethylammonium fluoride either alone or in combination with inorganic fluorides such as KF, $KHF_2$ in various proportion can also be employed.

In accordance with the present disclosure there is provided a process for the preparation of perfluoroalkyl sulfenyl chloride.

The process comprising the following steps:
Step one involves reacting a compound of formula [I]

wherein R represents an aromatic group with or without a substituent; and R' represents a halogen,
with at least one fluoride compound and thiophosgene in a solvent to obtain a reaction mass.

The aromatic group is at least one selected from the groups consisting of aromatic hydrocarbon, heterocyclic aromatic and polycyclic aromatic hydrocarbon.

In accordance with one of the embodiments of the present disclosure the aromatic group is aromatic hydrocarbon which is selected from the group consisting of benzene, toluene, o,p,m-xylene benzophenone, substituted benzophenone, acetophenone, substituted acetophenone, tri methyl benzene, tetra methyl benzene and penta methylbenzene.

In accordance with another embodiment of the present disclosure the aromatic group is heterocyclic aromatic which is selected from the group consisting of furan, pyridine, pyrazine, imidazole, pyrazole, oxazole and thiophene.

In accordance with still another embodiment of the present disclosure the aromatic group is polycyclic aromatic hydrocarbon which is selected from the group consisting of naphthalene, anthracene and phenanthrene.

Typically, the halogen is at least one selected from the group consisting of fluorine, chlorine, bromine and iodine.

In accordance with the present disclosure the compound of formula I is selected from the group consisting of ortho-chlorobenzyl chloride, para-chlorobenzyl chloride, 4-chloromethyl methylene dioxy benzene, 1-chloromethyl naphthalene, bis-2,4-chloromethyl toluene, tris 2,4,6-chloromethyl toluene, bis-9,10-chloromethyl anthracene and a mixture thereof.

In accordance with the preferred embodiment of the present disclosure the compound of formula I is preferably ortho-chlorobenzyl chloride, para-chlorobenzyl chloride and a mixture thereof.

The fluoride compound employed in the reaction is selected from the group consisting of potassium fluoride, potassium bifluoride, sodium fluoride, tetramethylammonium fluoride and benzyltrimethylammonium fluoride.

The proportion of fluoride compound used is about 3.6 mole to 6.0 mole per mole of compound of formula I.

Typically, the proportion of thiophosgene is about 1.2 mole to 2.0 mole per mole of compound of formula I.

In accordance with the present disclosure the solvent employed in the reaction is selected from the group consisting of acetonitrile, dichloromethane, sulfolane and carbon tetra chloride.

In accordance with the preferred embodiment of the present disclosure the solvent used in the reaction is acetonitrile and sulfolane.

The second step is pulverizing the reaction mass with the help of beads to obtain a mixture containing trifluoromethyl thiomethyl benzene derivative.

The third step is isolating the trifluoromethyl thiomethyl benzene derivative from the mixture followed by distilling the trifluoromethyl thiomethyl benzene derivative to obtain a purified trifluoromethyl thiomethyl benzene derivative In accordance with the present disclosure the trifluoromethyl thiomethyl benzene derivative is selected from the group consisting of ortho-chlorobenzyl trifluoromethyl sulphide, para-chlorobenzyl trifluoromethyl sulphide, 3,4-dioxy methylene benzyl trifluoromethyl sulfide, 1-naphthalene methyl trifluoromethyl sulfide, toluene-bis-2,4-methyl trifluoromethyl sulfide, toluene-tris-2,4,6-methyl trifluoromethyl sulfide and anthracene-bis 9,10-methyl trifluoromethyl sulfide.

In accordance with the preferred embodiment of the present disclosure the trifluoromethyl thiomethyl benzene derivative is ortho-chlorobenzyl trifluoromethyl sulphide.

The next step is dissolving the purified trifluoromethyl thiomethyl benzene derivative in a solvent selected from the group consisting of dichloromethane, toluene, benzene, ethylene dichloride, mono chloro benzene, carbon tetra chloride, ortho dichloro benzene and tri chloro benzene.

The last step is cleaving the trifluoromethyl thiomethyl benzene derivative by selective chlorinolysis by passing chlorine gas at a temperature in the range of about −18 to about 80° C. to obtain perfluoroalkyl sulfenyl chloride.

In accordance with the preferred embodiment of the present disclosure cleaving of trifluoromethyl thiomethyl benzene derivative is carried out at a temperature in the range of about −5° C. to about 50° C.

In accordance with the preferred embodiment of the present disclosure the perfluoroalkyl sulfenyl chloride is trifluoromethylsulfenyl chloride.

In accordance with the present disclosure it is found that use of combinations of the alkali fluorides in various molar quantities from 4.0 moles to 10.0 moles in the reaction results in conversion of around 1%. It is further observed that by employing spherogel or grinding beads in the reaction, the conversion was found to be greater than 90%.

In accordance with the present disclosure the beads are selected from the group consisting of glass beads, sand beads, stainless steel beads, zirconium oxide beads and titanium beads.

Typically, the size of the beads employed in the reaction is in the range of about 0.5 mm to about 10 mm.

Preferably, the size of the beads is in the range of about 0.5 mm to about 3 mm.

The proportion of beads employed in the reaction is 250 g to 1000 g per mole of compound of formula I.

In accordance with present disclosure the shape of the beads is selected from the group consisting of spherical, oval, oblong and round.

In accordance with the preferred embodiment of the present disclosure spherical beads are employed in the reaction.

In accordance with another aspect of the present disclosure there is provided a system for the preparation of perfluoroalkyl sulfenyl chloride.

Figure 1:
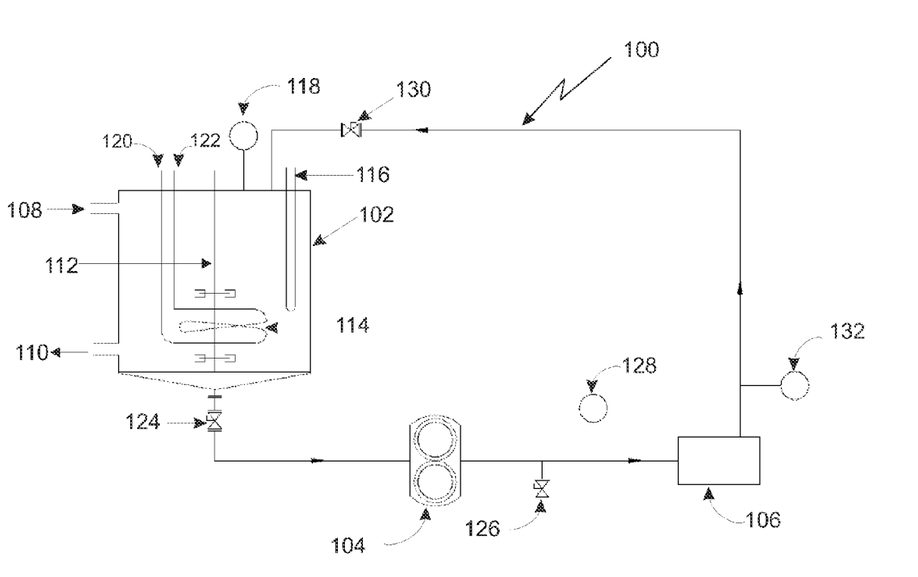
FIG. 1 illustrates a system for the preparation of perfluoroalkyl sulfenyl chloride

Referring to FIG. 1, a system 100 for preparation of perfluoroalkyl sulfenyl chloride is depicted. The system 100 includes a reactor 102, a pump 104 and a milling device 106. The reactor 102 includes an inlet means 108, an outlet means 110, a stirrer means 112, a cooling means 114, a temperature measuring and indicating means 116 and a pressure gauge 118.

The inlet means 108 is adapted for facilitating entry of reactants, such as acetonitrile, activated KF, ortho-chlorobenzyl chloride and thiophosgene into the reactor 102. The outlet means 110 is adapted for facilitating exit of the final product out of the reactor 102. The stirrer means 112 is adapted for mixing the reactants contained inside the reactor 102. In one embodiment of the present disclosure, the stirrer means 112 may include a pair of disc turbines configured thereon for better mixing and stirring of the reactants. The cooling means 114 is adapted for preventing overheating of the reactants during stirring and mixing operation. The cooling means 114 uses flow of cooling water for absorbing heat generated and thereby preventing overheating of the reactants during stirring and mixing operation. The cooling means 114 include a cooling water inlet 120 and a cooling water outlet 122. The temperature measuring and indicating means 116 is adapted for measuring and indicating the temperature of the resulting mixture of the reactants contained inside the reactor 102. The pressure gauge 118 is adapted for measuring pressure generated inside the reactor 102.

The pump 104 is adapted for moving the resulting mixture contained inside the reactor 102 to the milling device 106. The flow of the resulting mixture from the reactor 102 to the pump 104 may be regulated by a first valve 124. In one embodiment of the present disclosure, the pump 104 is a gear pump. However, the present disclosure is not limited to any particular type of pump used. Further, the flow of the resulting mixture from the pump 104 to the milling device 106 may regulated by a second valve 126. Also, the pressure of the resulting mixture from the pump 104 to the milling device 106 may be measured by a second pressure gauge 128.

The milling device 106 is adapted for pulverization of the resulting mixture moved from the gear pump 104. In one embodiment of the present disclosure, the milling device 106 is a bead mill. The bead mill 106 may include a plurality of beads to pulverize the resulting mixture moved from the pump 104. Further, the pulverized mixture from the milling mixture 106 enters into the reactor 102 for further mixing thereof in the reactor 102. The flow of the pulverized mixture from the milling device 106 to the reactor 102 may be regulated by the third valve 130. Further, the temperature of the pulverized mixture from the milling device 106 to the reactor 102 may be measured by a second temperature measuring and indicating means 132. Moreover, the final product formed after subsequent mixing in the reactor 102 is existed through the outlet means 110 of the reactor 102.

In accordance with the present disclosure it is observed that use of smaller beads having diameter size in the range of about 0.5 to 2 mm results in conversion greater than 98%. While use of bigger size spherogel or metallic beads results in lower conversion rate.

Therefore, in accordance with the preferred embodiment of the present disclosure metallic or glass beads having lower size are employed in the reaction. These lower size beads cause size reduction of solid particles and thereby increase surface area of the particles. This helps in appropriate mixing of the solid-liquid reactants and enhances the availability of anhydrous potassium fluoride in polar solvents which in turn results in high yield of the intermediate and final product at moderate reaction conditions.

Further, in the fluorination reactions which involve the use of thiophosegene and potassium fluoride and KHF2, the temperature is a critical parameter to determine the reaction yield and it is also necessary to keep the reaction temperature at a moderate level so that thiophosgene does not decompose at elevated temperature.

The present disclosure will now be described with respect to the following examples which do not limit the present disclosure in any way and only exemplify the present disclosure

EXAMPLES

Example 1

Anhydrous acetonitrile (2.0 liters), activated potassium fluoride (6.0 mole), Potassium bifluoride (0.3 mole) and ortho-chlorobenzyl chloride (1.0 mole) were charged in a glass reactor having a central vertical stirrer and a vertical condenser to obtain a reaction mass which was cooled to −15° C. To this chilled thiophosgene (1.2 mole) in 300 ml of acetonitrile was injected over a period of about 2 hours. The reaction mixture was then stirred for 2 hours and temperature of mixture was raised to 0° C. The reaction mixture was again stirred for 2 hours and temperature was raised to 30° C. followed by keeping the mixture for 2 hours. Thiophosgene 0.2 mole was injected into the reaction mixture and temperature of the mixture was raised to 80° C. and kept for 2 hours at 80° C. which was then cooled to 30° C. Further, thiophosgene (0.2 mole) was injected and the reaction temperature was raised to 80° C. After 10 hours only 1% conversion was observed. Even with further maintenance for several hours no further conversion was observed.

Example 2

Anhydrous acetonitrile (2.0 liters), tetramethylammonium fluoride (3.04 moles) and ortho-chlorobenzyl chloride (1.0 moles) were charged in a glass reactor having a central vertical stirrer and a vertical condenser to obtain a reaction mass which was cooled to −40° C. To this chilled thiophosgene (1.0 mole) in 300 ml of acetonitrile was injected over a period of about 2 hours. The reaction mixture was stirred for 2 hours and the temperature of the mixture was raised to 0° C. followed by stirring the reaction mixture for 2 hours. The temperature of the mixture was then raised to 30° C. and the mixture was kept for 2 hours. To this reaction mixture thiophosgene (0.2 mole) was injected and the temperature was raised to 80° C. The mixture was kept for 2 hours at 80° C. and then cooled to 30° C. Further, 0.2 mole of thiophosgene was injected and the temperature of the mixture was raised to 80° C. After 10 hours only 2% conversion was observed. Even with further maintenance for several hours no further conversion was observed.

Example 3

Anhydrous acetonitrile (2.0 liters), activated potassium fluoride (6.0 mole), Potassium bifluoride (0.3 mole), ortho-chlorobenzyl chloride (1.0 mole) and benzyltrimethylammonium fluoride (0.2 mole) were charged in a glass reactor having a central vertical stirrer. The process given in Example 1 was repeated. After 10 hours only 1% conversion was observed. Even with further maintenance for several hours no additional conversion was observed.

Example 4

Anhydrous acetonitrile (2.0 liters), tetramethylammonium fluoride (3.04 moles), ortho-chlorobenzyl chloride (1.0 moles) and benzyltrimethylammonium fluoride 0.2 mole were charged in a glass reactor having a central vertical stirrer. The process given in Example 1 was repeated. After 10 hours only 1% conversion was observed. Even with further maintenance for several hours no additional conversion was observed.

Example 5

Anhydrous acetonitrile (2.0 liters), activated KF (6.0 mole), $KHF_2$ (0.3 mole), ortho-chlorobenzyl chloride (1.0 mole) and 250 gm of spherogel with 2 mm diameter were charged in a glass reactor having a central vertical stirrer and a vertical condenser to obtain a reaction mass. The reaction mass was then cooled to −15° C. To this chilled thiophosgene (1.2 mole) in 300 ml of acetonitrile was injected into over a period of about 2 hours. The reaction mixture was stirred for 2 hours and the temperature was raised to 0° C. Then the reaction mixture was stirred for 2 hours. The temperature of the mixture was raised to 30° C. and the mixture was kept for 2 hours. To this thiophosgene (0.2 mole) was injected into the reaction mixture. The temperature of the mixture was then raised to 80° C. At this temperature mixture was kept for 2 hours and further cooled to 30° C. Again 0.2 mole of thiophosgene was injected to above mixture and the temperature of mixture was raised to 80° C. After 10 hours 80% conversion was observed. With further maintenance for 4 hours no additional conversion was observed. Ortho-chlorobenzyl trifluoromethyl sulphide was isolated from the mixture which was purified by distillation and subjected to chlorinolysis in Dichloromethane by passing chlorine gas at low temperature. The reaction was followed by GLC and terminated when the disappearance of starting material was observed, the reaction finally yielded trifluoromethylsulfenyl chloride. Yield: 96%.

Example 6

The process of example 5 was repeated except that the quantity of the spherogel used, was changed to 600 gm to obtain trifluoromethylsulfenyl chloride. Yield: 96%.

Example 7

Anhydrous acetonitrile (2.0 liters), activated KF (6.0 mole), ortho-chlorobenzyl chloride (1.0 mole) and 500 gm spherogel (2-3 mm diameter) were charged in a glass reactor having a central vertical stirrer and a vertical condenser to obtain a reaction mass. The reaction mass was then cooled to 0° C. To this chilled thiophosgene (1.2 mole) in 300 ml of acetonitrile was injected over 2 hours. The reaction mixture was stirred for 2 hours and the temperature of the mixture was raised to 10° C. Then the reaction mixture was stirred for 2 hours and the temperature was raised to 30° C. This mixture was kept for 2 hours. Thiophosgene (0.2 mole) was injected into the reaction mixture and the temperature was raised to 80° C. This mixture is kept for 2 hours at 80° C. and then cooled to 30° C. To this mixture thiophosgene (0.2 mole) was injected and the temperature of the mixture was raised to 80° C. The mixture was kept at the temperature until the GLC indicated absence of the starting material. ortho-chlorobenzyl trifluoromethyl sulphide was then isolated from the mixture and purified by distillation which is then subjected to chlorinolysis in dichloromethane by passing chlorine gas at 0 to 5° C. The reaction was followed by GLC and terminated when the disappearance of starting material was observed. The reaction yielded trifluoromethylsulfenyl chloride. Yield: 96%.

Example 8

The process of example 7 was repeated except that the SS-316 or SS-304 balls are used instead of spherogel. Yield: 96%.

Example 9

Anhydrous acetonitrile (2.0 liters), activated KF (6.0 mole), ortho-chlorobenzyl chloride (1.0 mole) and 500 gm SS-316 balls (2-3 mm diameter) were charged in a glass reactor having a central vertical stirrer and a vertical condenser to obtain a reaction mass which was then heated to 60° C. To this chilled thiophosgene (1.2 mole) in 300 ml of acetonitrile was injected over 2 hours. The reaction mixture was stirred for 2 hours. Thiophosgene 0.2 mole was injected into the reaction mixture which is then kept for 2 hours at 60° C. Further, thiophosgene 0.2 mole was injected and the reaction was maintained at 60° C. The mixture was kept at this temperature until the GLC indicated absence of the starting material. Ortho-chlorobenzyl trifluoromethyl sulphide was then isolated from the reaction mixture and purified by distillation (Boiling point 72° C./2 mm, 77° C./5 mm, 102° C./22 mm, product is confirmed by GC mass) which was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: 96%.

Example 10

Anhydrous acetonitrile (2.0 liters), activated KF (6.0 mole), $KHF_2$ (0.3 mole), ortho-chlorobenzyl chloride (1.0 mole) and 600 gm of zirconium oxide ball (1-2 mm diameter) were charged in a glass reactor having a central vertical stirrer and a vertical condenser.

The process of example 7 was repeated to obtain trifluoromethylsulfenyl chloride. Yield: 96%.

Example 11

Anhydrous Dichloromethane (2.0 liters), activated KF (6.0 mole), ortho-chlorobenzyl chloride (1.0 mole) and 500 gm spherogel (2-3 mm diameter) were charged in a glass reactor having a central vertical stirrer and a vertical condenser to obtain a reaction mass which was cooled to 0° C. To this chilled thiophosgene (1.2 mole) in 300 ml of dichloromethane was injected into the reaction mixture over 2 hours. The reaction mixture was stirred for 2 hours and the temperature was raised to 10° C. The reaction mixture was further stirred for 2 hours and the temperature was raised to 30° C. The mixture was kept for 2 hours. To this mixture 0.2 mole of thiophosgene was injected and the temperature was raised to 40° C. The mixture was kept at 40° C. for 2 hours and then cooled to 30° C. To this again 0.2 mole of thiophosgene was injected and the temperature was raised to 40° C. At this temperature mixture was kept for several hours. GLC indicated 24% conversion. Ortho-chlorobenzyl trifluoromethyl sulphide was then isolated from the mixture and purified by distillation which was further subjected to chlorinolysis in dichloromethane by passing chlorine gas at 0 to 5° C. The reaction was followed by GLC and terminated when the disappearance of starting material was observed. The reaction yielded trifluoromethylsulfenyl chloride. Yield: >96%.

Example 12

Anhydrous sulfolane (2.0 liters), activated KF (6.0 mole), KHF2 (0.3 mole), ortho-chlorobenzyl chloride (1.0 mole) and 600 gm of spherogel (2-3 mm diameter) were charged in a glass reactor having a central vertical stirrer and a vertical condenser. The process of example 10 was repeated. Yield: >96%.

Example 13

Anhydrous sulfolane (2.0 liters), activated KF (6.0 mole), KHF2 (0.3 mole), ortho-chlorobenzyl chloride (1.0 mole) and 600 gm of SS-316 balls or SS-304 balls (2-3 mm diameter) were charged in a glass reactor having a central vertical stirrer and a vertical condenser to obtain a reaction mass which was maintained at 30° C. To this chilled thiophosgene (1.2 mole) in 300 ml of Sulfolane as solvent was added over 4 hours. The reaction mixture was stirred for 2 hours and the temperature was raised to 60° C. Then the reaction mixture was stirred for 2 hours. To this mixture 0.2 mole of thiophosgene was injected and the temperature was raised to 65° C. The mixture was kept for 2 hours at 65° C. Further, 0.2 mole of thiophosgene was injected and the reaction mixture was kept at this temperature until the GLC indicated conversion to >98%. Ortho-chlorobenzyl trifluoromethyl sulphide was then isolated from the mixture and purified by distillation which was further subjected to chlorinolysis in dichloromethane by passing chlorine gas at 0 to 2° C. The reaction was followed by GLC and terminated when the disappearance of starting material was observed. The reaction yielded trifluoromethylsulfenyl chloride. Yield: >96%.

Example 14

Anhydrous dichloromethane (2.0 liters), activated KF (6.0 mole), KHF2 (0.3 mole), ortho-chlorobenzyl chloride (1.0 mole) and 600 gm of spherogel (2-3 mm diameter) were charged in a glass reactor having a central vertical stirrer and a vertical condenser to obtain a reaction mass which was cooled to 0° C. To this chilled thiophosgene (1.2 mole) in 300 ml of dichloromethane was added over 4 hours. The reaction mixture was stirred for 2 hours and the temperature was raised to 10° C. To this reaction mixture 0.2 mole of thiophosgene was injected and the temperature was raised to 45° C. The mixture was kept for 2 hours at 45° C. and then cooled to 30° C. To this 0.4 mole of thiophosgene was injected and the temperature of the mixture was raised to 45° C. The mixture was kept at this temperature for several hours. GLC indicated 30% conversion. Ortho-chlorobenzyl trifluoromethyl sulphide was then isolated from the mixture and purified by distillation which was subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 15

The following are charged in a glass reactor having a central vertical stirrer and a vertical condenser:
Anhydrous Acetonitrile (2.0 liters), activated KF (6.0 mole), KHF2 (0.3 mole), ortho-chlorobenzyl chloride (1.0 mole), 600 gm spherogel (2-3 mm diameter), thiophosgene (1.2 mole) in 300 ml of Acetonitrile as solvent, is added over 4 hours at 30° C. The reaction mixture is stirred for 2 hours and the temperature is raised to 50° C., Thiophosgene 0.2 mole is injected into the reaction mixture, over 2 hours, maintained at 50° C. for 2 hours. Injected 0.2 mole thiophosgene over 2 hours & raised temperature to 65° C. & maintained. GLC indicated Conversion to be >96%. Ortho-chlorobenzyl trifluoromethyl sulphide is isolated and purified by distillation and subjected to chlorinolysis in dichloromethane by passing chlorine gas at 0 to 5° C., the reaction was followed by GLC and terminated when the disappearance of starting material is observed. The reaction yielded trifluoromethylsulfenyl chloride. Yield: >96%.

Example 16

Anhydrous Acetonitrile (2.0 liters), activated KF (6.0 mole), KHF2 (0.3 mole), ortho-chlorobenzyl chloride (1.0 mole) and 600 gm of spherogel (2-3 mm diameter) were charged in a glass reactor having a central vertical stirrer and a vertical condenser. To this thiophosgene (1.2 mole) in 300 ml of acetonitrile was added over 4 hours at 60° C. The reaction mixture was stirred for 2 hours. Then 0.2 mole of thiophosgene was injected into the reaction mixture over 2 hours and the mixture was maintained at 60° C. for 2 hours. To this 0.2 mole of thiophosgene was injected over 2 hours and the temperature of the mixture was raised to 65° C. The mixture was maintained at 65° C. GLC indicated >96% conversion. Ortho-chlorobenzyl trifluoromethyl sulphide was isolated and purified by distillation which was then subjected to chlorinolysis in Dichloromethane by passing chlorine gas at low temperature. The reaction was followed by GLC and terminated when the disappearance of starting material was observed. The reaction yielded trifluoromethylsulfenyl chloride. Yield: >96%.

Example 17

Anhydrous Acetonitrile (2.0 liters), activated KF (6.0 mole), ortho-chlorobenzyl chloride (1.0 mole) and 600 gm of spherogel (2-3 mm diameter) were charged in a glass reactor having a central vertical stirrer and a vertical condenser.

The process of example 16 was repeated. Yield: >96%.

Example 18

Anhydrous Acetonitrile (2.0 liters), activated NaF (6.0 mole), KHF2 (0.3 mole), ortho-chlorobenzyl chloride (1.0 mole) and 600 gm of spherogel (2-3 mm diameter) were charged in a glass reactor having a central vertical stirrer and a vertical condenser. To this thiophosgene (1.2 mole) in 300 ml of acetonitrile was added over 4 hours at 60° C. The reaction mixture was stirred for 2 hours and then 0.2 mole of thiophosgene was injected into the reaction mixture over 2 hours. The mixture was maintained at 60° C. for 2 hours. To this 0.2 mole of thiophosgene was injected over 2 hours and the temperature of the mixture was raised to 65° C. The mixture was kept at this temperature for several hours. GLC indicated 15% conversion. Ortho-chlorobenzyl trifluoromethyl sulphide was isolated from the mixture and purified by distillation which was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 19

The process of example 9 was repeated except that acetonitrile solvent with 0.3% moisture was employed instead of anhydrous acetonitrile.
The conversion was found to be 75%. Ortho-chlorobenzyl trifluoromethyl sulphide was isolated and purified by distillation and subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 20

The process of example 9 was repeated except that acetonitrile solvent with 1% moisture was employed instead of anhydrous acetonitrile.
The conversion was found to be 30%. Ortho-chlorobenzyl trifluoromethyl sulphide was isolated and purified by distillation and subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 21

Anhydrous acetonitrile (2.0 liters), ortho-chlorobenzyl chloride (1.0 mole), KF (6 moles) and KHF2 (0.3 mole) were charged in a glass reactor having a central vertical stirrer and a vertical condenser. This reactor was connected to bead mill by slurry pump and discharged of bead mill was connected back to the reactor. (FIG. 1)
The reaction mass was agitated and heated to 55° C. With the help of slurry pump, mass was pumped in to the bead mill and circulation was started. To this thiophosgene (1.2 mole) in 300 ml of acetonitrile was injected over 4 hours. The reaction mixture was stirred for 2 hours and the temperature was maintained at 60° C. Thiophosgene 0.2 mole was injected into the reaction mixture at 60° C. The temperature was then raised to 65° C. and the mixture was kept for 2 hours at 65° C. The mixture was then cooled to 60° C. To this 0.2 mole of thiophosgene was injected and the reaction mixture was kept at this temperature until the GLC indicated the absence of the starting material. Ortho-chlorobenzyl trifluoromethyl sulphide was then isolated from the mixture and purified by distillation which was subjected to chlorinolysis in dichloromethane by passing chlorine gas at −5 to 0° C. The reaction was followed by GLC and terminated when the disappearance of starting material was observed. The reaction yielded trifluoromethylsulfenyl chloride. Yield: 96%.

Example 22

Anhydrous acetonitrile (2.0 liters), ortho-chlorobenzyl chloride (1.0 mole) and KF (3.5 moles) were charged in a glass reactor having a central vertical stirrer and a vertical condenser. The process of example 21 was repeated. Yield: 96%.

Example 23

Anhydrous carbon tetrachloride (CTC) (2.0 liters), activated KF (6.0 mole), ortho-chlorobenzyl chloride (1.0 mole) and 500 gm of spherogel (2-3 mm diameter) were charged in a glass reactor having a central vertical stirrer and a vertical condenser to obtain a reaction mass which was then kept at 30° C. To this thiophosgene (1.2 mole) in 300 ml of CTC was injected over 2 hours. The reaction mixture was stirred for 2 hours and the temperature was raised to 40° C. To this reaction mixture 0.2 mole of thiophosgene was injected and the temperature of the mixture was raised to 60° C. The mixture was kept for several hours. GLC indicated 25% conversion. Ortho-chlorobenzyl trifluoromethyl sulphide was isolated and purified by distillation which was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 24

Anhydrous Acetonitrile (2.0 liters), activated KF (6.0 mole), ortho-chlorobenzyl chloride (1.0 mole) and 923 gm of SS balls (2 mm diameter) were charged in a glass reactor having a central vertical stirrer and a vertical condenser. To this 1.2 mole of thiophosgene in 300 ml of acetonitrile was added over 4 hours at 60° C. The reaction mixture was stirred for 2 hours. GLC indicated 99% conversion. Ortho-chlorobenzyl trifluoromethyl sulphide was isolated from the mixture and purified by distillation which was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 25

The process of example 24 was repeated except that the quantity of the SS-304 or 316 balls used was 700 gm instead of 923 gm. The reaction was followed by GLC and terminated when the disappearance of starting material was observed. The reaction yielded trifluoromethylsulfenyl chloride. Yield: >96%.

Example 26

The process of example 24 was repeated except that the quantity of the SS balls used was 600 gm instead of 923 gm. The reaction was followed by GLC and terminated when the disappearance of starting material was observed. The reaction yielded trifluoromethylsulfenyl chloride. Yield: >96%.

Example 27

Anhydrous acetonitrile (2.0 liters), activated KF (6.0 mole) and ortho-chlorobenzyl chloride (1.0 mole) were charged in a glass reactor having a central vertical stirrer and a vertical condenser to obtain a reaction mass which was then heated to 60° C. To this reaction mixture, chilled thiophosgene (1.2 mole) in 300 ml of acetonitrile was injected over 2 hours. The reaction mixture was stirred for 2 hours. The conversion was found to be negligible. To this added 500 gm of SS balls and the mass was stirred for 2 hours at 60° C. The GLC conversion was found to be 30%. Thiophosgene (0.2 mole) was then injected and the reaction mixture was maintained at 60° C. The mixture was kept at the same temperature for 2 hours. GLC indicated 45% conversion. With further maintenance no further conversion was observed. Ortho-chlorobenzyl trifluoromethyl sulphide was isolated and purified by distillation which was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: >96%.

Example 28

Anhydrous acetonitrile (2.0 liters), activated KF (6.0 mole), 4-chloromethyl methylene dioxy benzene (1.0 mole) and 600 gm of SS balls (2 mm diameter) were charged in a glass reactor having a central vertical stirrer and a vertical condenser. To this mixture 1.2 mole of thiophosgene in 300 ml of acetonitrile was added over 4 hours at 60° C. The reaction mixture was then stirred for 2 hours. GLC indicated 70% conversion. The product 3,4-dioxy methylene benzyl trifluoromethyl sulfide was isolated and purified by distillation. Product was confirmed by GC mass. The product was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: 90%.

Example 29

Anhydrous acetonitrile (2.0 liters), activated KF (6.0 mole), 1-chloromethyl naphthalene (1.0 mole) and 600 gm of SS balls (2 mm diameter) were charged in a glass reactor having a central vertical stirrer and a vertical condenser. To this mixture 1.2 mole of thiophosgene in 300 ml of acetonitrile was added over 4 hours at 60° C. The reaction mixture was stirred for 2 hours. GLC indicated 65% conversion. Product 1-naphthalene methyl trifluoromethyl sulfide was confirmed by GC Mass. The product was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: 80%.

Example 30

Anhydrous acetonitrile (2.0 liters), activated KF (10.0 mole), Bis-2,4-chloromethyl toluene and tris 2,4,6-chloromethyl toluene in the g ratio of 90:10 (1.0 mole), and 800 gm of SS balls (2 mm diameter) were charged in a glass reactor having a central vertical stirrer and a vertical condenser. To this 3.0 mole of thiophosgene in 300 ml of acetonitrile was added over 4 hours at 60° C. The reaction mixture was stirred for 2 hours. GLC indicated 65% conversion. Products namely toluene, bis-2,4-methyl trifluoromethyl sulfide and toluene, tris-2,4,6-methyl trifluoromethyl sulfide were confirmed by GC Mass. The product was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: 70%.

Example 31

Anhydrous acetonitrile (2.0 liters), activated KF (10.0 mole), Bis-9,10-chloromethyl anthracene (1.0 mole) and 800 gm SS balls (2 mm diameter) were charged in a glass reactor having a central vertical stirrer and a vertical condenser. To this thiophosgene (2.5 mole) in 300 ml of acetonitrile was added over 4 hours at 66° C. The reaction mixture was stirred for 2 hours. GLC indicated 65% conversion. Product anthracene, bis 9,10-methyl trifluoromethyl sulfide was confirmed by GC Mass. The product was then subjected to chlorinolysis in dichloromethane by passing chlorine gas at low temperature. The reaction was followed by GLC and terminated when the disappearance of starting material was observed. The reaction yielded trifluoromethylsulfenyl chloride. Yield: 70%.

Example 32

The process of example 9 was repeated except that 6 mole NaF per mole was used instead of 6 mole KF per mole. No conversion was observed.

Example 33

Anhydrous sulfolane (1.50 liters), activated KF (5.0 mole), p-chlorobenzyl chloride (1.0 mole), 600 gm spherogel (2-3 mm diameter) were charged in a glass reactor having a central vertical stirrer and a vertical condenser. To this thiophosgene (1.2 mole) in 200 ml of Sulfolane was added over 4 hours at 60° C. The reaction mixture was stirred for 2 hours and the temperature was raised to 65° C. Thiophosgene 0.25 mole was injected into the reaction mixture and kept at 65° C. until the GLC indicated conversion to >95%. p-chlorobenzyl trifluoromethyl sulphide was isolated and purified by distillation (Bpt 69-70° C./7 mm Hg) and subjected to chlorinolysis in EDC by passing chlorine gas at low temperature. The reaction was followed by GLC and terminated when the disappearance of starting material was observed. The reaction yielded trifluoromethylsulfenyl chloride in >95% yield.

Example 34

Anhydrous sulfolane (1.50 liters), activated KF (4.50 mole), ortho chlorobenzyl chloride & p-chlorobenzyl chloride in the mole ratio 60:40 (total 1.0 mole), 600 gm spherogel (2-3 mm diameter) were charged in a glass reactor having a central vertical stirrer and a vertical condenser. To this thiophosgene (1.2 mole) was added over 4 hours at 60° C. The reaction mixture was stirred for 2 hours and the temperature is raised to 65° C. Thiophosgene 0.25 mole was injected into the reaction mixture and kept at 65° C. until the GLC indicated conversion to >95%. Mixture of p-chlorobenzyl trifluoromethyl sulphide & o-chloro trifluromethyl sulfide was isolated by distillation (BP 86-88° C./10 mm Hg) and subjected to chlorinolysis in EDC by passing chlorine gas at low temperature. The reaction was followed by GLC and terminated when the disappearance of starting material was observed. The reaction yielded trifluoromethylsulfenyl chloride in >95% yield.

Example 35

Anhydrous sulfolane (1.50 liters), activated KF (4.50 mole), ortho chlorobenzyl chloride & p-chlorobenzyl chloride recovered after chlorinolysis of OCBTMS/PCBTMS in the mole ratio 60:40 (total 1.0 mole) and 600 gm spherogel (2-3 mm diameter) were charged in a glass reactor having a central vertical stirrer and a vertical condenser: To this thiophosgene (1.2 mole) was added over 4 hours at 60° C. The reaction mixture was stirred for 2 hours and the temperature was raised to 65° C. Thiophosgene 0.25 mole was injected into the reaction mixture and kept at 65° C. until the GLC indicated conversion to >95%. Mixture of p-chlorobenzyl trifluoromethyl sulphide & o-chloro trifluromethyl sulfide was isolated by distillation (BP 86-88° C./10 mm Hg) and subjected to chlorinolysis in EDC by passing chlorine gas at low temperature. The reaction was followed by GLC and terminated when the disappearance of starting material was observed. The reaction yielded trifluromethylsulfenyl chloride in 95% yield.

Effect of Solvent and Temperature Conditions on Conversion:

The results are shown in table No 1.

TABLE 1

| Sr. No. | Example No. | Solvent | KF m/m | Quantity of SS ball or spherogel | Temp ° C. | Conversion |
|---|---|---|---|---|---|---|
| 1 | 24 | Acetonitrile (2.3 lit) | 6 | 923 gm (SS ball) | 60 | 99% |
| 2 | 25 | Acetonitrile (1.7 lit) | 4.5 | 700 gm (SS ball) | 60 | 99% |
| 3 | 26 | Acetonitrile (1.4 lit) | 3.6 | 600 gm (SS ball) | 60 | 95% |
| 4 | 5 | Acetonitrile (2.3 lit) | 6 | 250 gm (SS ball) | −15 to 60 | 80% |
| 5 | 9 | Acetonitrile | 6 | 500 gm (SS ball) | 60 | 96% |
| 7 | 13 | Sulfolane | 6 | 600 gm (SS ball) | 30 | 98% |
| 6 | 11 | Dichloromethane | 6 | 500 gm (spherogel) | 60 | 24% |
| 8 | 23 | Carbon tetra chloride | 6 | 600 gm (spherogel) | 30 | 25% |

Effect of Moisture on Conversion:

The results are shown in table No 2.

TABLE 2

| Sr. No. | Example No. | Solvent/ moisture | KF m/m | Quantity of SS ball | Temp. ° C. | Conversion |
|---|---|---|---|---|---|---|
| 1 | 9 | Acetonitrile (2.3 lit)/0.05% | 6 m/m | 500 gm | 60 | 99% |
| 2 | 19 | Acetonitrile (2.3 lit)/0.3% | 6 m/m | 500 gm | 60 | 75% |
| 3 | 20 | Acetonitrile (2.3 lit)/1% | 6 m/m | 500 gm | 60 | 30% |

While considerable emphasis has been placed herein on the specific steps of the preferred process, it will be appreciated that many steps can be made and that many changes can be made in the preferred steps without departing from the principles of the present disclosure. These and other changes in the preferred steps of the present disclosure will be apparent to those skilled in the art from the disclosure herein, whereby it is to be distinctly understood that the foregoing descriptive matter is to be interpreted merely as illustrative of the present disclosure and not as a limitation.

The invention claimed is:

1. A process for the preparation of perfluoroalkyl sulfenyl chloride; said process comprising the following steps:
   a. reacting a compound of formula [I]

wherein R represents an aromatic group, with or without a substituent; and R' is selected from the group consisting of fluorine and chlorine;
   with at least one fluoride compound selected from the group consisting of potassium fluoride, potassium bifluoride, sodium fluoride, tetramethylammonium fluoride and benzyltrimethylammonium fluoride and thiophosgene in a solvent selected from the group consisting of acetonitrile, dichloromethane, sulfolane and carbon tetrachloride, to obtain a reaction mass containing trifluoromethyl thiomethyl benzene derivative;
   b. pulverizing the reaction mass with beads having a size of about 0.5 mm to about 3 mm and isolating the trifluoromethyl thiomethyl benzene derivative from the reaction mass;
   c. distilling the trifluoromethyl thiomethyl benzene derivative to obtain a purified trifluoromethyl thiomethyl benzene derivative;
   d. dissolving the purified trifluoromethyl thiomethyl benzene derivative in a solvent selected from the group consisting of dichloromethane, toluene, benzene, ethylene dichloride, mono chloro benzene, carbon tetra chloride, ortho dichloro benzene and tri chloro benzene; and e. cleaving the trifluoromethyl thiomethyl benzene derivative by selective chlorinolysis by passing chlorine gas at a temperature in the range of about −10° C. to about 50° C. to obtain a perfluoroalkyl sulfenyl chloride with a yield of greater than 90%.

2. The process as claimed in claim 1, wherein the aromatic group is selected from the group consisting of aromatic hydrocarbon, heterocyclic aromatic and polycyclic aromatic hydrocarbon.

3. The process as claimed in claim 2, wherein the aromatic hydrocarbon is selected from the group consisting of benzene, toluene, ortho-xylene, para-xylene, meta-xylene, benzophenone, substituted benzophenone, acetophenone, substituted acetophenone, tri methyl benzene, tetra methyl benzene and penta methylbenzene.

4. The process as claimed in claim 2, wherein the heterocyclic aromatic group is selected from the group consisting of furan, pyridine, pyrazine, imidazole, pyrazole, oxazole and thiophene.

5. The process as claimed in claim 2, wherein the polycyclic aromatic hydrocarbon is selected from the group consisting of naphthalene, anthracene and phenanthrene.

6. The process as claimed in claim 1, wherein the compound of formula I is selected from the group consisting of ortho-chlorobenzyl chloride, para-chloro benzyl chloride, 4-chloromethyl methylene dioxy benzene, 1-chloromethyl naphthalene, bis-2,4-chloromethyl toluene, tris 2,4,6-chloromethyl toluene and bis-9, 10-chloromethyl anthracene.

7. The process as claimed in claim 1, wherein the solvent employed in step (a) is selected from the group consisting of acetonitrile, sulfolane, and a combination thereof.

8. The process as claimed in claim 1, wherein the trifluoromethyl thiomethyl benzene derivative is selected from the group consisting of ortho-chlorobenzyl trifluoromethyl sulphide, para-chlorobenzyl trifluoromethyl sulphide, 3,4-dioxy methylene benzyl trifluoromethyl sulfide, 1-naphthalene methyl trifluoromethyl sulfide, toluene-bis-2,4-methyl trifluoromethyl sulfide, toluene-tris-2,4,6-methyl trifluoromethyl sulfide and anthracene-bis 9, 10-methyl trifluoromethyl sulfide.

9. The process as claimed in claim 1, wherein the solvent employed in step (d) is selected from the group consisting of dichloromethane, ethylene dichloride, and a combination thereof.

10. The process as claimed in claim 1, wherein the cleaving of the trifluoromethyl thiomethyl benzene derivative is carried out at a temperature in the range of about −5° C. to 50° C.

11. The process as claimed in claim 1, wherein the perfluoroalkyl sulfenyl chloride is trifluoromethylsulfenyl chloride.

12. The process as claimed in claim 1, wherein the yield of perfluoromethyl sulfenyl chloride is at least 94%.

13. The process as claimed in claim 1, wherein the beads are selected from the group consisting of glass beads, sand beads, stainless steel beads, titanium beads and zirconium oxide beads.

14. The process as claimed in claim 1, wherein the proportion of beads employed in the reaction is 0.25 kg to 1 kg per mole of compound of formula I.

15. The process as claimed in claim 1, wherein the shape of the beads is selected from the group consisting of spherical, oval and round.

16. The process as claimed in claim 1, wherein the proportion of fluoride compound used is 3.6 moles to 6.0 moles per mole of compound of formula I.

17. The process as claimed in claim 1, wherein the proportion of thiophosgene is 1.2 moles to 2.0 moles per mole of compound of formula I.

* * * * *